(12) United States Patent
Smith

(10) Patent No.: US 9,120,861 B2
(45) Date of Patent: Sep. 1, 2015

(54) FUNCTIONAL ENHANCEMENT OF ANTIMICROBIALS

(75) Inventor: James Leif Smith, West Point, MS (US)

(73) Assignee: Mississippi State University, Mississippi State, MS (US)

( * ) Notice: Subject to any disclaimer, the term of this patent is extended or adjusted under 35 U.S.C. 154(b) by 741 days.

(21) Appl. No.: 12/589,115

(22) Filed: Oct. 16, 2009

(65) Prior Publication Data

US 2010/0145010 A1    Jun. 10, 2010

Related U.S. Application Data

(60) Provisional application No. 61/196,505, filed on Oct. 17, 2008.

(51) Int. Cl.
  *C07K 14/00* (2006.01)
  *C07K 14/315* (2006.01)

(52) U.S. Cl.
  CPC ............... *C07K 14/315* (2013.01); *C07K 14/00* (2013.01)

(58) Field of Classification Search
  CPC .............................. C07K 14/00; C07K 14/315
  USPC .................................... 530/324, 326; 514/2.4
  See application file for complete search history.

(56) References Cited

U.S. PATENT DOCUMENTS

| 4,036,833 | A | * | 7/1977 | Ishimaru et al. | ............... 540/226 |
| 5,545,721 | A | * | 8/1996 | Carroll et al. | ............... 530/391.7 |
| 5,763,395 | A | * | 6/1998 | Blackburn et al. | ............... 514/2.4 |
| 6,086,921 | A | * | 7/2000 | Domenico | .................... 424/653 |

OTHER PUBLICATIONS

Lees (Journal of Veterinary Pharmacology and Therapeutics 27(6) 397-414, 2004).*
Goodman and Gilmans' Manual of Pharmocology & Therapeutics 2008 (pp. 1-25).*

* cited by examiner

*Primary Examiner* — David Lukton
(74) *Attorney, Agent, or Firm* — Lawrence Arthur Schemmel

(57) ABSTRACT

The present invention provides methods for adding functional hydrophobic, charge, polar, and other structural groups on antimicrobial compounds for enhancing the physicochemical properties of the antimicrobial compounds, thereby creating novel antimicrobial analogs with enhanced functions.

10 Claims, 9 Drawing Sheets

Type A Lantibiotics

```
                   *+ * ++       +    *    + ++ +      *
Nisin A            ITSISLCTPGCKTGALMGCNMKTATCHCSIVHSK
Nisin Z            ITSISLCTPGCKTGALMGCNMKTATCNCSIVHSK
Subtilin           WKSESLCTPGCVTGALQTCFLQTLTCNCKT--SK
                    + * ++   +  *  +  + +#
Mutacin 1140       FKSWSLCTPGCARTGSFNSYCC
Epidermin          IASKFICTPGCAKTGSFNSYCC
Gallidermin        IASKFLCTPGCAKTGSFNSYCC
Staphyloccin T     IASKFLCTPGCAKTGSFNSYCC
Mutacin β-NY266    FKSWSFCTPGCAKTGSFNSYCC
```

FUNCTIONAL ENHANCEMENT OF ANTIMICROBIALS

CROSS-REFERENCE TO RELATED APPLICATION

This application claims priority from U.S. Provisional Patent Application Ser. No. 61/196,505 filed Oct. 17, 2008. The entirety of that provisional application is incorporated herein by reference.

FIELD OF THE INVENTION

This invention relates to the field of antibiotics and more specifically to the field of lantibiotics and involves methods of adding functional hydrophobic, charge, polar, and other structural groups on antimicrobial compounds containing alpha beta unsaturated carbonyls, whereby such groups enhance the physical and chemical (physicochemical) properties of the antimicrobial compounds.

BACKGROUND OF THE INVENTION

The present invention provides novel methods in designing synthetic antibiotic analogs with enhanced antimicrobial and therapeutic properties. One of many particularly interesting groups of antimicrobials that could benefit from the proposed modifications is called lantibiotics.

The present invention in a preferred embodiment utilizes natural lantibiotic products, synthetic lantibiotic products, or mutagenized lantibiotic products for the subsequent chemical addition of a thiol compound carrying a novel functional group and includes antimicrobial compounds containing an alpha beta unsaturated carbonyl group labeled with a thiol compound.

Lantibiotics are antimicrobial peptides that have potential usefulness in treating infectious diseases. They are known to have a potent and broad spectrum of activity, an insignificant cytotoxicity, and demonstrated efficacy in animal infection models, suggesting therapeutic potential.

The present invention provides a novel and distinctive technology called functional enhancement of antimicrobials (FEAM) that provides novel methods for the manufacture of novel lantibiotic analogs with enhanced functions and novel antimicrobial compounds that have enhanced properties. Enhancement of the antimicrobial compounds refers to improvements in the physical and chemical (physicochemical) properties. The premise for this technology involves understanding that defined and undefined constraints on lantibiotics prevent nature from making the most effective bactericidal compound. A single addition of a functional group, such as a charge group, polar group, or a hydrophobic group can have significant effects on the bioactivities, pharmacokinetics, and/or pharmacodynamics of an antimicrobial compound. As described herein, 2,3-didehydroalanine (Dha) and 2,3 didehydrobutyrine (Dhb) residues are commonly found in lantibiotics, as well as other ribosomally and non-ribosomally synthesized antimicrobials. The present invention makes use of the alpha, beta unsaturated carbonyl group found in these residues, which lend themselves to the addition of thiol compounds containing novel functional groups in a highly selective fashion. The single step additions are easily optimized and can be made in aqueous solvents with greater than a 90% yield. Furthermore, Dha and Dhb residues are easily engineered in lantibiotics by site directed mutagenesis or by an organosynthesis method, further facilitating the production of unique analogs with enhanced functions. The invention provides for the creation of novel lantibiotic analogs that contain a reactive carboxyl group or amino group which facilitates the addition of other functional groups using standard coupling chemistry.

A need exists in the field of antibiotics, and specifically lantibiotics, for a method of enhancing the pharmacokinetic and the pharmacodynamic activity of antimicrobial compounds. The present invention provides such a method.

SUMMARY OF THE INVENTION

The present invention provides for novel methods of creation and generation of novel antimicrobial analogs with enhanced functions. The invention provides for the creation of novel antibiotic analogs that contain a reactive carboxyl group which facilitates the addition of other functional groups using standard coupling chemistry. Additionally, the present invention provides for novel analogs containing a polar group including but not limited to mercatoethanol having higher bioavailability than the native compound and analogs with hydrophobic groups including but not limited to ethanethiol and thiophenol, wherein such analogs have improved antimicrobial activities.

With the foregoing and other objects, features, and advantages of the present invention that will become apparent hereinafter, the nature of the invention may be more clearly understood by reference to the following detailed description of the preferred embodiments of the invention and to the appended claims.

BRIEF DESCRIPTION OF THE DRAWINGS

These drawings accompany the detailed description of the invention and are intended to illustrate further the invention and its advantages:

FIG. 1 is a graphical illustration of the sequence alignment of Type A (I) lantibiotics belonging to the nisin A and mutacin 1140 structural group.

DETAILED DESCRIPTION OF THE INVENTION

Lantibiotics are antimicrobial peptides that have potential usefulness in treating infectious diseases. They are known to have a potent and broad spectrum of activity, an insignificant cytotoxicity, and demonstrated efficacy in animal infection models, suggesting therapeutic potential.

Figure 2:
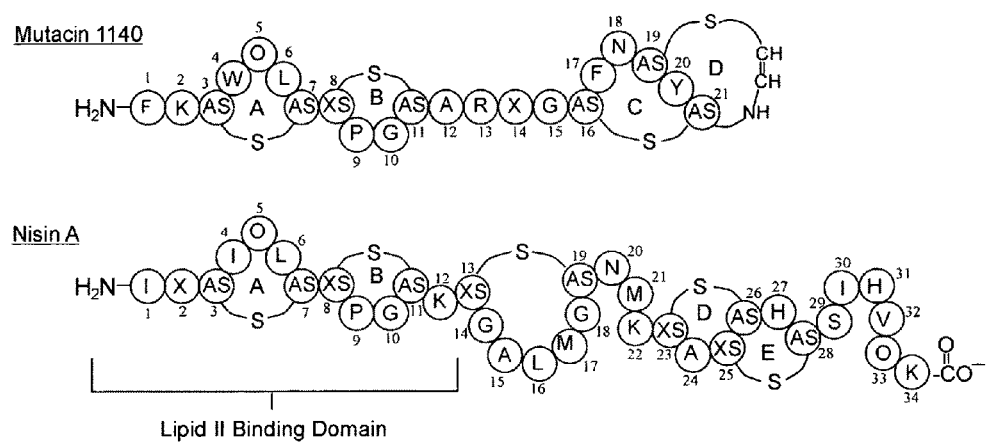
FIG. 2 is a graphical illustration of the covalent structures of nisin A and mutacin 1140.
Figure 3:
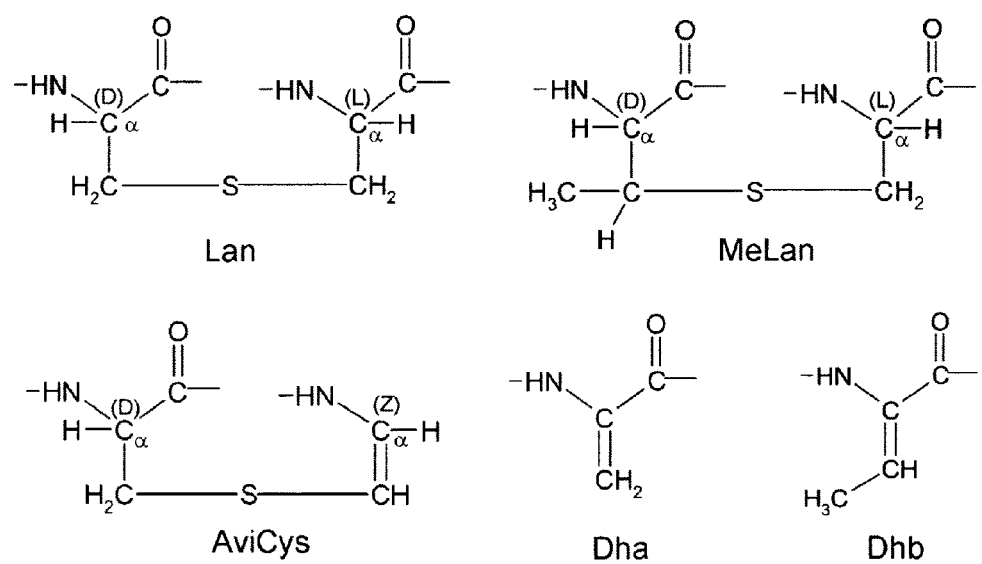
FIG. 3 is a graphical illustration of the structure of the modified residues in Type A (I) lantibiotics of nisin and mutacin 1140 subgroup.

A general discussion of lantibiotic structure and synthesis can provide a basic understanding of these compounds. Five (5) subclasses of lantibiotics exist based on differences in their chemistry and biosynthesis: (1) Type A (I); (2) Type A (II); (3) Type B; (4) Two-Component; and (5) those of unknown structures. Type A (I) lantibiotics (Class I bacteriocins) fall into two subgroups: (1) those that are structurally similar to nisin A (van de Ven 1991 and Gross 1971), which is produced by *L. lactis*; and (2) those that share structural similarities to mutacin 1140 (smith 2000), which is a peptide that is naturally produced by a strain of the common oral bacterium *Streptococcus mutans*. FIG. 1 shows the sequence alignment of Type A (I) lantibiotics belonging to the Nisin A and mutacin 1140 structural group. A considerable amount of similarity exists between the first eleven amino acids in the nisin A and mutacin 1140 group, represented by the dumbbell. Amino acid residues of interest are in bold. Residues in bold with an asterisk symbol above the column represent amino acids involved in thioether linkages. Residues in bold with a plus symbol above the column represent the location of the dehydrated residues 2,3-didehydroalanine (Dha) and 2,3-didehydrobutyrine (Dhb) containing an alpha beta unsaturated carbonyl group. The residues that are decarboxylated are in bold with a pound (number) symbol above the column. FIG. 2 shows the representation of the covalent structures of nisin A and mutacin 1140. The circles represent amino acids. The one letter designation is given for each amino acid. One letter code for each standard amino acid is listed in the circles that represent the amino acid positions. Non-standard amino acids are listed as "O" which is 2,3-didehydroalanine (Dha), "X" which is 2,3 didehydrobutyrine (Dhb), "AS" which is a component of the lanthionine residue, and "XS" which is the methyl component of the β-methyl lanthionine residue. Gram positive bacteria are responsible for biosynthesis of the known lantibiotics. Lantibiotics are rich in the sulfur-containing amino acids, lanthionine (Lan, ala-S-ala) and frequently 3-methyl-lanthionine (MeLan, abu-S-ala). The occurrence of the unusual amino acids lanthionine (Lan) and β-methyl-lanthionine (MeLan) define lantibiotics and give them their name. In addition to the Lan and MeLan residues, there may be other post-translationally modified amino acids. Some of the other modified amino acids found in mutacin 1140 include 2,3-didehydroalanine (Dha), 2,3 didehydrobutyrine (Dhb), and the unsaturated lanthionine derivatives such as S-amino vinyl-D-cysteine (AviCys) (FIG. 3). FIG. 3 shows the structure of the modified residues derived from the bacterial synthesis of lantibiotics in the type A (I) lantibiotics of nisin and mutacin 1140 subgroup. The Lan rings C and D are intertwined in mutacin 1140 subgroup of lantibiotics, further adding to the complexity of these molecules.

Figure 4:
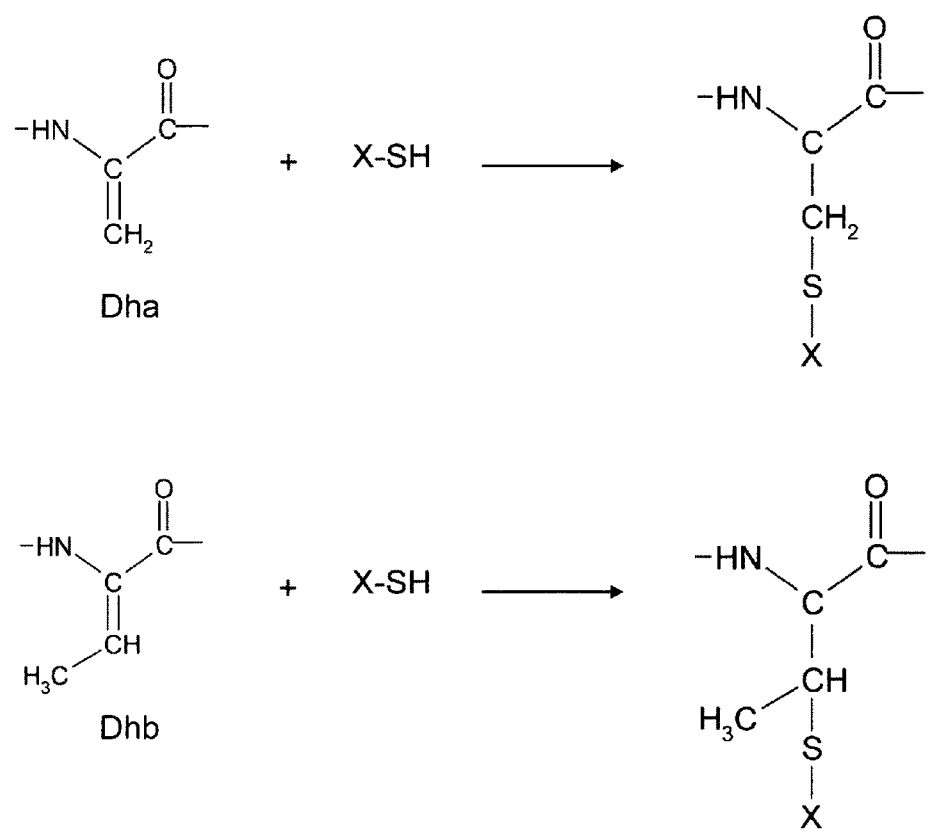
FIG. 4 is an illustration of the Dha and Dhb residues commonly found in ribosomally and non-ribosomally synthesized antimicrobials.

The present invention (FEAM) provides novel methods for the manufacture of novel antibiotic analogs. The premise for the invention is based upon the knowledge that defined and undefined constraints on antimicrobial compounds prevent natural processes from making the most effective antimicrobial compound. For example, in the case of the lantibiotic nisin, conformational constraints required for its interaction with the lantibiotic synthetase enzymes, immunity gene product, and membrane receptor for its autoinducing activity, may prevent it from evolving into the most effective antibiotic. The single addition of a functional group, such as a charge group, polar group, or a hydrophobic group, can have significant effects on the bioactivities, pharmacokinetics, and/or pharmacodynamics of an antimicrobial compound. For example, ring A of nisin shows mutational freedom and the incorporation of a positive charge or a hydrophobic group by site directed mutagenesis has a profoundly positive effect on the spectrum of activity and level of antimicrobial activity against some target bacterial species when compared to wild-type nisin (Rink 2007). Moreover, 2,3-didehydroalanine (Dha) and 2,3 didehydrobutyrine (Dhb) residues as shown in FIG. 3 and FIG. 4 are commonly found in ribosomally synthesized antimicrobials (such as lantibiotics) and in non-ribosomally synthesized antimicrobials. The present invention makes use of the alpha, beta unsaturated carbonyl group found in these residues, which lend themselves to the addition of thiol compounds containing novel functional groups in a highly selective fashion. The single step additions are easily optimized and can be made in aqueous and organic solvents with greater than a 90% yield. Dha and Dhb residues are easily engineered in ribosomally-produced antimicrobials, such as lantibiotics, by site directed mutagenesis or by an organosynthesis method, further facilitating the production of unique analogs with enhanced functions.

The present invention provides for novel compositions as shown in FIG. 4 whereby ribosomally and non-ribosomally synthesized antimicrobial compounds containing 2,3-didehydroalanine (Dha) and 2,3 didehydrobutyrine (Dhb) residues are labeled with an organosulfur compound (X—SH). The "X" designates the chemical composition of the thiol organosulfur compound (functional group) added to enhance the properties of the antimicrobial agent.

In one embodiment of the present invention, the method includes the addition of a thiol organosulfur compound to an antimicrobial compound that enhances the spectrum of activity of the antimicrobial compound. Altering the antimicrobial compound by the addition of a functional group can have significant effects on the minimum inhibitory concentrations (MICs) of these antimicrobial compounds against a panel of select organisms.

In another embodiment of the present invention, differences in the effective rates of addition of thiol compounds to 2,3-didehydroalanine (Dha) and 2,3 didehydrobutyrine (Dhb) residues, or residue combinations thereof, enable dual addition of select thiol compounds to a peptide scaffold with or resulting in a high yield of desired product. Peptide scaffold refers to a peptide antibiotic being used as the base in which new peptide antibiotic analogs can be derived. The desired product comprises the labeled antimicrobial compound with two thiol organosulfur compounds.

In yet another embodiment of the present invention, the method includes the addition of a thiol organosulfur compound to an antimicrobial compound that alters at least one of the physical properties of the antimicrobial compound and that results in reducing in vitro toxicity and acute toxicity in test organisms.

In yet another embodiment of the present invention, the method includes the addition of a thiol organosulfur compound to an antimicrobial compound that alters at least one of the physical properties of the antimicrobial compound and that eliminates preexisting antimicrobial resistance and delays the development of new genetically stable resistance pathogens.

In a further embodiment of the present invention, the method includes the addition of a thiol organosulfur compound to an antimicrobial compound that alters at least one of the physical properties of the antimicrobial compound and that enhances the pharmacodynamics (PD) and the pharmacokinetics (PK) parameters of the antimicrobial compound. Antimicrobial compounds with an attached functional group may enhance in vivo efficacy of the antimicrobial compounds. Alteration of the antimicrobial compounds can have a positive effect on peak plasma concentration ($C_{max}$), time to peak plasma concentration ($T_{max}$), elimination half-life ($t_{1/2}$), the volume of distribution ($V_d$), clearance (Cl), and mean residence time (MRT) of the antimicrobial compounds.

In yet another embodiment of the present invention, the method includes the addition of a thiol organosulfur compound to an antimicrobial compound that alters at least one of the physical properties of the antimicrobial compound and that enhances the protein binding properties of the antimicrobial compound. Protein binding can affect the antimicrobial compound drug's distribution, tissue penetration, metabolism, and elimination from the body. Only the unbound antimicrobial compound drug in serum is likely to elicit a pharmacologic effect. However, an antimicrobial compound drug bound to serum can have a positive effect on the half life of the compound. Therefore, functional groups can be engineered into an antimicrobial compound that will optimize the protein binding properties of the compound.

In a further embodiment of the present invention, the method includes the addition of a thiol organosulfur compound to an antimicrobial compound that alters at least one of the physical properties of the antimicrobial compound and that enhances the chemotherapeutic and antiviral properties of the antimicrobial compound. Antimicrobial compounds show immense promise in the treatment of cancer. Furthermore, many antimicrobial compounds show promise as antiviral compounds. The addition of a thiol organosulfur compound to an antimicrobial compound will enable the synthesis of analogs that may be effective against cancer and viral infections.

In yet another embodiment of the present invention, the method includes the purification of active pharmaceutical ingredients (APIs), such as antimicrobials containing an alpha, beta unsaturated carbonyl group, from a complex mixture of organic and inorganic compounds. Semi-purified products can be labeled with an organosulfur compound that will facilitate a final purification step. For instance, this process includes, but is not limited to, the addition of an organosulfur tag for affinity chromatography purification.

In yet a further embodiment of the present invention, novel organosulfur compounds can be used that contain additional functional groups to enable supplementary chemistry coupling reactions. For example, thiolactic acid or aminothiophenol contains a carboxyl and amino group, respectively, which enables the use of standard coupling chemistry. Additional novel compounds containing reactive functional groups can be utilized in the synthesis of novel organosulfur compounds that can be added to antimicrobial compounds, thus promoting an additional level of unique analogs that can be produced.

In another embodiment of the present invention, novel organosulfur compounds can be engineered that enable the production of a selective antimicrobial compound. Given the adverse effects antimicrobials can have on an animal's microbial flora, which often leads to other opportunistic infections, novel antimicrobial compounds may be engineered that are selective for a particular pathogen.

In yet another embodiment of the present invention, novel organosulfur compounds, labeled with isotope carbon-14, can be added to an antimicrobial compound containing an alpha, beta unsaturated carbonyl group. This addition will enable "microdosing" studies, which are designed to determine how the body of an animal or human responds to a drug.

Mutacin 1140 was previously chemically modified with 2-mercaptoethanol at neutral pH to selectively label only existing dehydrated residues (Dha5 and Dhb14) in a set of experiments designed to characterize its covalent structure. The sample (12 µL, ~15 µg) was incubated in 0.1M ammonium acetate buffer pH 7 with 2-mercaptoethanol (3 µL) at 50° C. for 1 h and then analyzed by ESI-MS and MS/MS (Smith 2003). Further improvements of the procedure demonstrate that it is easily scalable for large-scale industrial synthesis of novel compounds. Most reactions will occur in aqueous solutions at room temperature in a time-dependent manner (yield >90%). Optimization of the organosulfur labeling should be conducted for each antimicrobial compound containing an alpha, beta unsaturated carbonyl group. The choice of solvent for reaction will depend upon the relative solubility of the thiol organosulfur compound and the antimicrobial compound. Labeling can occur in aqueous, buffered aqueous, aqueous:organic, and organic solvent mixtures. In one embodiment, choice of solvent for the lantibiotic mutacin and nisin was buffered water when using water soluble organosulfur compound β-mercaptoethanol, ethanethiol, and thiolactic acid.

We utilized a similar approach to synthesize a number of chemical variants of mutacin 1140 by labeling the dehydrated amino acids with thiol organosulfur compounds. Ammonium acetate buffer was not the best buffer to use for the reaction and most likely would not provide sufficient buffering capacity as we scaled this procedure up to make milligram quantities of thiol mutacin derivatives. Under acidic pH conditions, the thioether linkages would become susceptible to breakage by the addition of the thiol organosulfur compounds. Therefore it was important to maintain pH above 7.0 throughout the reaction. Tris buffer (200 mM) (Tris(hydroxymethyl)-aminomethane) was useful in these buffered reactions since it has a pKa value of 8.06 at 25° C. Thiol organosulfur additions were expected to readily occur at room temperature and this was the base temperature for our reaction optimizations.

Conditions for thiol organosulfur labeling: (1) Solvent conditions for obtaining optimal solubility of the antimicrobial compound should be determined, taking into consideration the solvent solubility of the organosulfur compound. An organosulfur compound with a poor solubility profile can be added in a time-dependent manner, in accordance to the time required for the reaction to run to completion. In our work, 200 mM concentration of Tris buffer (pH 8.5) provided sufficient buffering capacity. The reaction volume was 1.5 mL in a 5 mL glass vial purged with nitrogen gas. (2) Molar ratios of the antimicrobial compound (mutacin 1140) and thiol organosulfur compound should be optimized for complete labeling of the dehydrated residues, ratio concentrations being 1:2, 1:5, 1:10, 1:20, 1:50, and 1:100 of alpha, beta unsaturated carbonyl groups found in the antimicrobial compound to thiol organosulfur (1:5, 1:10, 1:20 mM of mutacin 1140 to thiol organosulfur). The ratio that gives the best yield of desired product, as can be ascertained by RP-HPLC and MALDI, in a 30-minute reaction can be used for the next steps of optimization. Furthermore, these reactions can also be done in parallel with samples that contain guanidine HCl to determine whether this will facilitate labeling of buried alpha, beta unsaturated carbonyl groups by denaturing the tertiary conformation. (3) The next variable to be optimized should be time, while keeping the reaction mixture at room temperature (~25° C.). Reactions can be checked at 30-minute intervals by RP-HPLC and MALDI. (4) Optimizing the rate of the reaction can be done by increasing the temperature by 5° C. intervals to find the optimal temperature and time. If the reaction goes to a non-permissive temperature for the antimicrobial compound or organosulfur compound, the ratio of the thiol organosulfur compound can be raised. (5) When necessary, the reaction can be stopped by adjusting the pH or by solvent extraction. The thiol organosulfur compounds will be soluble in the ether, while the antimicrobial compound, in general, will remain in the aqueous phase. In our work, once the thiol organosulfur was removed, the samples were loaded onto RP-HPLC on a 10×250 mm C18 column and purified.

The chemical derivatives of mutacin 1140 were used in characterization of the mutacin's bioactivity. It is important to make a distinction between bioactivity and bactericidal activity. Bioactivity refers to mutacin's ability to self assemble into complexes, bind to lipid II, orientate itself properly in membranes, and its bactericidal activity, whereas bactericidal activity refers only to mutacin 1140's ability to kill bacteria. We investigated bioactivity changes as it pertained to lipid II binding, complex formation, membrane binding, and bactericidal activity against *M. luteus* (a mutacin 1140 indicator strain). The thiol organosulfur can be bought isotopically labeled (2H, 13C, 15N), such as 2-propene-1-thiol, 2-thiazoline-2-thiol, 4-aminothiophenol, ethanethiol; and sodium methane thiolate, and sodium borohydride. Isotopically labeled forms enabled us to determine the relative effect that these modifications have on mutacin 1140 interaction with bacterial-mimetic membranes. Also of particular interest was the thiol organosulfur compound 4-aminothiophenol. This compound has an available amino group for attaching a fluorescent tag that would enable confocal microscopy experiments designed to visualize mutacin 1140 in biological membranes. Similarly, thiolactic acid has an available carboxyl group that will be available for the addition of a fluorescent tag, as well as functional peptide tags. For these reasons, the above thiol organosulfur compounds were used for engineering the structural variants of mutacin 1140. Some of these derivatives alter the compounds' spectrum of bactericidal activity, solubility, and/or toxicity.

With the ability to engineer a hybrid-mutacin 1140 molecule, or other hybrid lantibiotic molecules, it may eventually be possible to engineer specifically-targeted antimicrobial peptide (STAMP) lantibiotics, similar to what was previously done against *S. mutans* by engineering an eight amino acid linker known to target a membrane protein involved in *S. mutans* competence to the peptide antibiotic novispirin G10 (Eckert 2006). This hybrid peptide antibiotic had increased selectivity for *S. mutans* and enhanced ability to kill *S. mutans* in biofilms. Similar approaches can be developed with mutacin 1140 as well as other antibiotics containing an alpha, beta unsaturated carbonyl group, in which the antibiotic could be engineered to specifically target a bacterial pathogen of choice or possibly contain a specific synthetically or non-synthetically derived peptide construct that would facilitate localization of the antibiotic in the liver and/or kidneys or move it across the blood brain barrier. The use of an antibiotic labeled with thiolactic acid or possibly other thiol compounds containing an available carboxyl group or amino groups would enable standard coupling of such a peptide to the antimicrobial compound.

EXAMPLES

Figure 5:
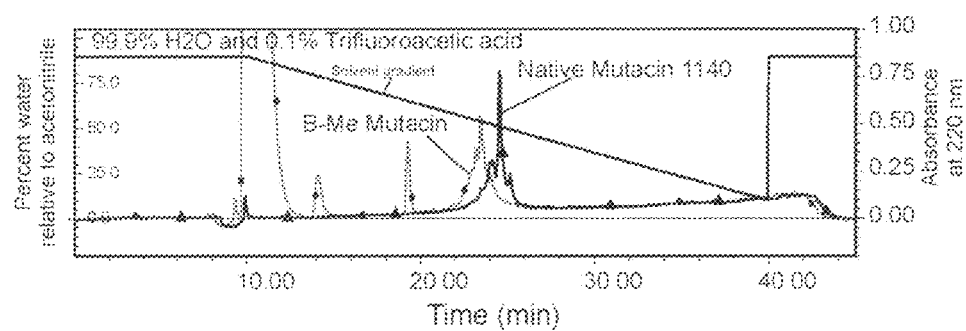
FIG. 5 is a graphically illustration of an RP-HPLC chromatogram of native mutacin 1140 overlaid on the chromatogram of 2-mercaptoethanol modified mutacin 1140 (B-Me mutacin).
Figure 6:
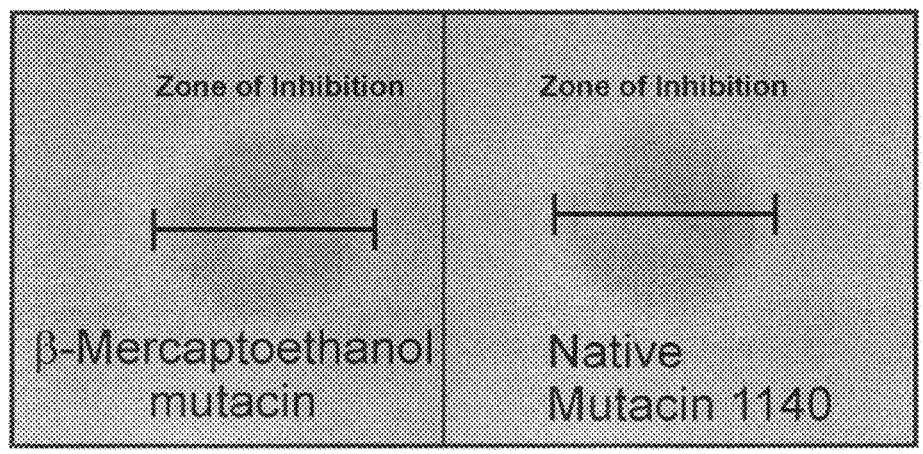
FIG. 6 is a representation of a 5 µL sample of native mutacin 1140 and B-Me mutacin onto a plate overlaid with *M. luteus*, showing that the B-Me mutacin modified sample retains a significant amount of bactericidal activity.
Figure 7:
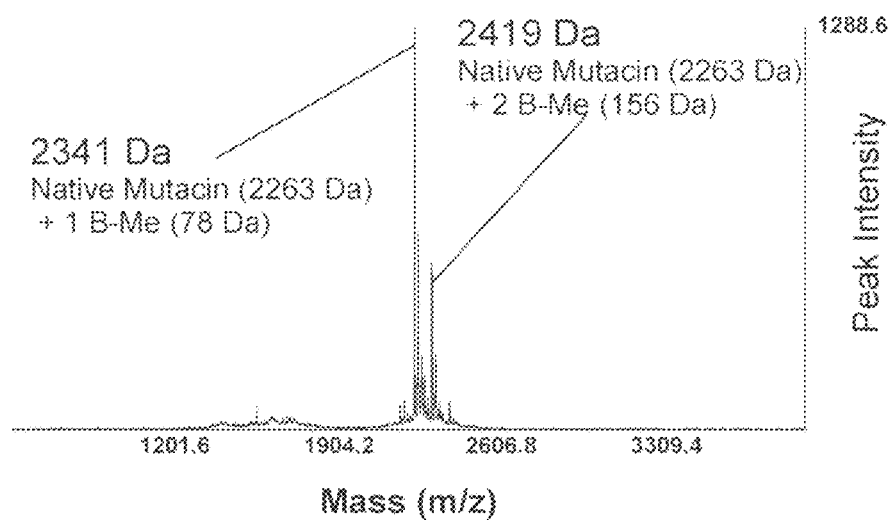
FIG. 7 is a graphical illustration showing that the mass of the B-Me mutacin modified sample was determined by MALDI and contained two main isotopic masses of 2341 and 2419 corresponding to the addition of 1 and 2 mercaptoethanols.

We performed a 2-mercaptoethanol addition to mutacin 1140 at pH 7.3 in Tris buffer at room temperature for 2 hours. The results of this experiment to show "proof of principle" for our organosulfur chemistry experiments are shown in FIGS. 5, 6, and 7. FIG. 5 is a RP-HPLC chromatogram of the native mutacin 1140, designated by the black line with triangles, overlaid on the chromatogram of the 2-mercaptoethanol modified mutacin 1140 (B-Me mutacin), which is designated by the grey line with circles. The modification changes the retention time of the native molecule to the left, a slightly more hydrophilic solvent (more water relative to acetonitrile). The large peak in the flow through was determined, by smell, to be 2-mercaptoethanol. The two small sharp peaks following the flow peak, which both have an absorbance in the 280 nm range, appears to be contaminants in the 2-mercaptoethanol solution. They also appeared in Nisin A modified by the same 2-mercaptoethanol labeling procedure. Nisin has no aromatic residues to account for this absorbance. Nisin A also retains its bioactivity following thiol addition. In the future, these 2-mercatoethanol peaks will be removed by washing the sample with ice cold ether, which will extract the thiol compound leaving our peptide in solution. We spotted 5 μL of the native mutacin and the B-Me mutacin onto a plate overlaid with *M. luteus*. The results can be seen in FIG. 6, which shows a bacterial clearing (inhibition of bacterial growth) attributed to the addition of the compounds to the bioassay plate. The B-Me modified sample still retains a significant amount of bactericidal activity in this assay. The mass of the B-Me mutacin was determined by MALDI and was shown to contain two main isotopic masses of 2341 and 2419 (FIG. 7), corresponding to the addition of 1 and 2 mercaptoethanols. Interestingly, as seen by MALDI, nisin had three additions of 2-mercaptoethanol, corresponding to the three dehydrated residues Dhb2, Dha5, and Dha33. There were no signs of a plus one or plus two addition of 2-mercaptoethanol in the labeled nisin sample, suggesting that these dehydrated residues are more accessible to thiol labeling than the Dhb14 residue in mutacin 1140. We also performed the same reaction with ethanethiol following the same procedure outline above. This reaction resulted in a shift to the right on the RP-HPLC chromatogram. The bioassay was complicated, since the MALDI data showed the presence of a single addition of ethanethiol and the presence of native mutacin 1140. This reaction would presumably have to go for a longer period of time or higher temperature than that of 2-mercaptoethanol.

Addition of organosulfur compounds to the lantibiotics mutacin 1140, nisin A, and gallidermin does not interfere with the antibiotics ability to bind to lipid II. This is interesting because both nisin A and mutacin 1140 are labeled in ring A of the molecule, which interacts with lipid II (FIG. 2). Presumably, the orientation in which the organosulfur compound is attached points away from the lipid II binding pocket. In all instances, mutacin 1140, nisin A, and gallidermin are still bioactive peptides following addition of organosulfur compounds. Gallidermin contains a single 2,3 didehydrobutyrine (Dhb) residue at amino acid position fourteen in the lantibiotic hinge region, which is a flexible region of the antimicrobial peptide located between thioether rings A & B and rings C & D. Thiolactic acid addition has enhanced antimicrobial activity (>4-fold increase) against the mutacin 1140 indicator strain *Micrococcus luteus*. These preliminary studies demonstrate that antimicrobials, like the lantibiotics described above, are amendable to chemical modification and that addition of unique functional groups via organosulfur labeling can have profound effects on the function of an antimicrobial. In essence, this technology facilitates the production of unique antibiotics by using the natural products containing 2,3-didehydroalanine (Dha) and 2,3 didehydrobutyrine (Dhb) residues as scaffolds for the addition of unique thiol compounds. Peptide scaffold refers to a peptide antibiotic being used as the base in which new peptide antibiotic analogs can be derived, particularly using Dha and Dhb residues for the addition of unique thiol compounds. Furthermore, the present invention demonstrates that the lantibiotics mutacin 1140, gallidermin and nisin, are potential antibiotic scaffolds from which novel antibiotics can be derived.

Figure 8:
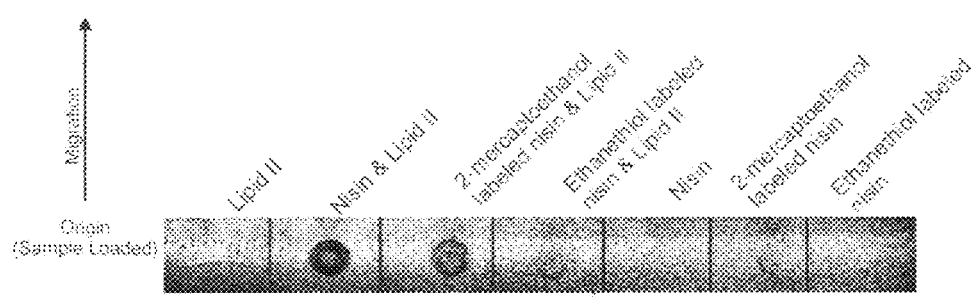
FIG. 8 is a graphical illustration of the origins (where sample is spotted on the plate) of thin layer chromatography (TLC) plates that demonstrate that nisin maintains lipid II binding activity following addition of organosulfur compounds mercaptoethanol and ethanethiol.
Figure 9:
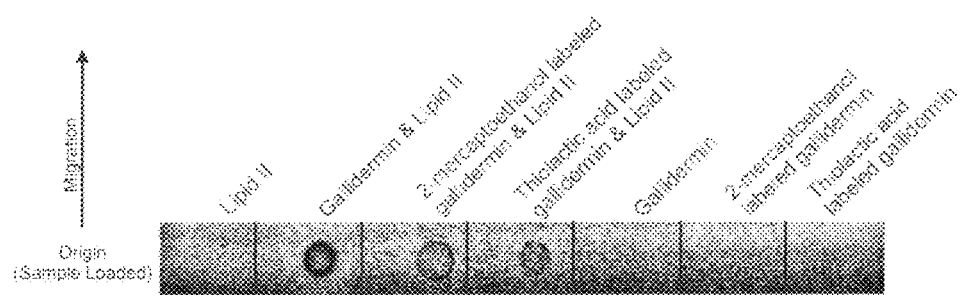
FIG. 9 is a graphical illustration of the origins (where sample is spotted on the plate) of thin layer chromatography (TLC) plates that demonstrate that gallidermin maintains lipid II binding activity following addition of organosulfur compounds mercaptoethanol and thiolactic acid.

In FIG. 8 and FIG. 9, a thin layer chromatography (TLC) lipid II binding assay for native and modified nisin A and gallidermin is shown, respectively. The method of the present invention enables direct visualization for the loss of lipid II binding. The native antibiotic nisin and gallidermin retain lipid II at the origin of the TLC plate, while lipid II spotted on its own migrates away from the origin (no visible iodine stain). Each antibiotic is spotted by itself to demonstrate that it does not stain with iodine. Each chemical variant retains its ability to bind to lipid II, albeit ethanethiol labeled nisin appears to have a diminished capacity to retain lipid II at the origin. Nisin is not as stable as gallidermin at higher temperatures. Thus, this observation may also be attributed to possible degradation of nisin scaffold during the chemical modification procedure and indicates that the reaction may need to be further optimized.

The present invention provides the necessary information for the development of hybrid mutacin 1140 analogs and unique antibiotic analogs with enhanced functions. Moreover, some or all of these novel analogs may have more desirable and enhanced pharmacokinetic and pharmacodynamic properties that make them more attractive therapeutic agents.

This disclosure has for the first time described and fully characterized a method for adding functional hydrophobic, charge, polar, and other structural groups on antimicrobial compounds containing alpha beta unsaturated carbonyls to enhance the physicochemical properties of the antimicrobial compounds.

The above detailed description is presented to enable any person skilled in the art to make and use the invention. Specific details have been disclosed to provide a comprehensive understanding of the present invention and are used for explanation of the information provided. These specific details, however, are not required to practice the invention, as is apparent to one of ordinary skill in the art. Descriptions of specific applications, analyses, and calculations are meant to serve only as representative examples. Various suitable changes, modifications, combinations, and equivalents to the preferred embodiments may be readily apparent to one skilled in the art and the general principles defined herein may be applicable to other embodiments and applications while still remaining within the spirit and scope of the invention. The claims and specification should not be construed to unduly narrow the complete scope of protection to which the present invention is entitled. It should also be understood that the figures are presented for example purposes only. No intention exists for the present invention to be limited to the embodiments shown and the invention is to be accorded the widest possible scope consistent with the principles and features disclosed herein.

What is claimed is:

1. In a method of treating a microbial infection, the method comprising administering to a subject in need thereof an antimicrobial compound that contains a 2,3-didehydroalanine (Dha) or 2,3-didehydrobutyrine (Dhb) moiety, or a combination thereof, the improvement comprising increasing the half-life of the antimicrobial compound in the subject by a method comprising treating said antimicrobial compound with at least one thiol-bearing compound for a time and under conditions effective to form a covalent adduct between said thiol-bearing compound and said antimicrobial compound, wherein said thiol-bearing compound contains an additional reactive functional group, and administering said covalent adduct to said subject.

2. The method of claim 1, wherein said additional reactive functional group is an amino group or a carboxyl group.

3. The method of claim 1, wherein said additional reactive functional group is a charged group, a polar group, a hydrophobic group, or a combination of two or more thereof.

4. The method of claim 1, wherein the at least one thiol-bearing compound is labeled with isotope carbon-14 for determining the response of the subject to the antimicrobial compound.

5. The method of claim 1, wherein the antimicrobial compound comprises at least one alpha, beta unsaturated carbonyl group.

6. The method of claim 1 wherein the microbial infection is bacterial, and the antimicrobial compound is an antibacterial agent.

7. The method of claim 6 wherein the improvement further comprises increasing the potency of said antibacterial agent.

8. The method of claim 1, wherein said conditions comprise reacting the thiol-bearing compound and the antimicrobial compound in a reaction mixture, wherein the rate of the reaction is optimized by adjusting the temperature of the reaction mixture as well as the molar ratio of the thiol-bearing compound to the antimicrobial compound.

9. The method of claim 8, wherein the molar ratio that is achieved is determined in part by the solubility of the thiol-bearing compound and of the antimicrobial compound in the reaction mixture.

10. In a method of treating an infection by a microbial species, the method comprising administering to a subject in need thereof an antimicrobial compound that contains a 2,3-didehydroalanine (Dha) or 2,3-didehydrobutyrine (Dhb) moiety, or a combination thereof, the improvement comprising mitigating preexisting antimicrobial resistance and delaying the onset of new resistant microbial species, wherein said improvement is achieved by a method comprising treating said antimicrobial compound with at least one thiol-bearing compound for a time and under conditions effective to form a covalent adduct between said thiol-bearing compound and said antimicrobial compound, wherein said thiol-bearing compound contains an additional reactive functional group, and administering said covalent adduct to said subject.

* * * * *